United States Patent [19]
Wang et al.

[11] Patent Number: 5,567,282
[45] Date of Patent: Oct. 22, 1996

[54] ON-CAPILLARY ELECTROPHORETIC IMMUNOSUBTRACTION FOR CLASSIFICATION AND TYPING OF M-PROTEINS

[76] Inventors: Hann-Ping Wang, 5230 Via Primaria, Yorba Linda, Calif. 92686; Cheng-Ming Liu, 5855 Via Del Bisonte, Yorba Linda, Calif. 92687

[21] Appl. No.: 186,347
[22] Filed: Jan. 25, 1994
[51] Int. Cl.$^6$ .................................................. C25B 7/00
[52] U.S. Cl. ........................... 204/450; 204/601; 436/516
[58] Field of Search ........................... 204/182.8, 299 R; 436/516

[56] References Cited

U.S. PATENT DOCUMENTS 5,228,960  7/1993  Liu et al. .............................. 204/182.8

*Primary Examiner*—John Niebling
*Assistant Examiner*—C. Delacroix-Muirheid

[57] ABSTRACT

A method for classifying and typing M-proteins present in a sample of serum, etc. of an individual is disclosed. The method employs an on-capillary electrophoretic immunosubtractive method to analyze and classify identified M-proteins.

25 Claims, 1 Drawing Sheet

ON-CAPILLARY ELECTROPHORETIC IMMUNOSUBTRACTION FOR CLASSIFICATION AND TYPING OF M-PROTEINS

FIELD OF THE INVENTION

The invention relates to an improved method for classifying and typing M-proteins present in a sample of serum, etc. of an individual. More specifically, it relates to the use of an homogeneous aqueous on-capillary electrophoretic immunosubtractive analysis to effect such classification and typing.

BACKGROUND OF THE INVENTION:

I. M-Protein

Antibodies are a class of immunoglobulins that are capable of recognizing and binding "foreign" (or antigenic) molecules that invade mammals and other vertebrates. A typical antibody consists of a pair of two "heavy" chains linked to a pair of two identical "light" chains to form a hypothetical "Y" structure. The heavy chains form the base of the "Y," and the light chains form the two branches. The heavy chains and light chains are separately synthesized by the immune system. There are two types of light chains, referred to as "kappa" ("κ") and "lambda" ("λ"). Similarly, there are several classes of heavy chains: γ ("IgG"); α (IgA); δ ("IgD"); μ ("IgM") and ε ("IgE"). IgG, IgA and IgM are the major serum immunoglobulins; IgD and IgE are generally present in serum only at very low concentrations.

The IgM immunoglobulin differs from other classes of immunoglobulins in that it is a pentamer of the basic four-chain antibody. It thus contains five "Y" structures, each of which has 2 light and 2 heavy chains. The monomeric units of IgM are held together by disulfide bonds, and by a single polypeptide, known as the "J chain." Free, monomeric M-protein is not found in healthy individuals, but rather is a distinguishing feature of a number of diseases and conditions (Bush, S. T. et al., *J. Lab. Clin. Med.* 73:194–201 (1969)).

Indeed, in healthy individuals, the synthesis of the antibody chains is synchronized by the immune system, such that under normal circumstances, only complete immunoglobulins are produced. Upon encountering an antigen, the B-cells of the immune system clonally proliferate to ensure the production of a sufficient amount of immunoglobulins to neutralize the invading antigen. After the invasion has been neutralized, the production of the immunoglobulins typically ceases. Occasionally, however, unregulated B-cell clones will escape regulation, and continue to produce immunoglobulin even after the antigen has been eliminated. The immunoglobulins of such cells have the same antigen binding site, suggesting that the cells reflect the clonal proliferation of a single ancestor cell. The immunoglobulins produced by such cells are referred to as monoclonal immunoglobulins, or "M-proteins."

The production of such M-proteins can reflect the presence of serious disease. Multiple myeloma, for example, is associated with the production of IgG, IgA, IgD, IgM or IgE M-proteins. A major pathologic feature of multiple myeloma is bone destruction, i.e., bone deformity or acute, painful pathological fractures. Clinically, the patient may experience bone pain, infections due to decreased production of normal Ig's, and anemia. Twenty percent of myeloma patients evidence Bence Jones protein, which is a free monoclonal light chain. Multiple myeloma can also impact neural tissue (i.e., the spinal cord, nerve roots and cranial or peripheral nerves).

The production of IgM M-proteins is associated with rheumatoid arthritis, certain immunodeficiency diseases, infective diseases, and B cell lymphoproliferative disorders, such as multiple myeloma, Waldenström's macroglobulinemia and lymphoma (Ishii, H., *Acta. Med. Okayama* 42:279–286 (1988); Roberts-Thomson, P. J. et al., *Austr. NZ J. Med.* 14:121–125 (1984); Carter, P. M. et al., *Br. Med. J.* 2:260–261 (1971); Harris-Dangkul, V. et al., *J. Immunol.* 155:216–222 (1977)). Its presence in such diseases may amount to between 10–40% of the total IgM concentration (Roberts-Thomson, P. J. et al., *Austr. NZ J. Med.* 14:121–125 (1984)), and the overall expression of the protein appears to correlate with the clinical significance of such diseases (Nagai, K. et al., *Scand. J. Immunol.* 14:99–108 (1981); Ishii, H., *Acta. Med. Okayama* 42:279–286 (1988)). The increased production of IgM increases the viscosity of the patient's blood (causing "hyperviscosity"), and is associated with headache, dizziness and vertigo.

The heavy chain composition (i.e., IgA, IgG, IgM, IgE, IgD) of an M-protein defines that protein's class. The light chain composition (κ or λ) of the protein defines its type. The classification and typing of an M-protein is of substantial clinical value and importance, and a variety of approaches have been used to classify and type M-proteins. For example, serum M-protein levels have been determined using column chromatography (Sugai, S. et al., *Jpn. J. Clin. Oncol.* 13:533–542 (1983); Roberts-Thomson, P. J. et al., *Austr. NZ J. Med.* 14:121–125 (1984)), cellulose acetate electrophoresis (Ishii, H., *Acta. Med. Okayama* 42:279–286 (1988); Sezaki, T. et. al., *Jpn. J. Clin. Hematol.* 23:847–853 (1982)), agarose gel electrophoresis (Beckman Instruments Inc. Paragon System), capillary electrophoresis methods (U.S. Pat. No. 5,228,960), and by hemolytic plaque assays (Nagai, K. et al., *Scand. J. Immunol.* 14:99–108 (1981)). An ELISA for M-proteins has also been developed (Sugai, S. et al., *Jpn. J. Clin. Oncol.* 13:533–542 (1983)). In this assay, M-protein is coupled to glass beads and permitted to react with rabbit anti-M-protein antibodies, followed by reaction with peroxidase-conjugated goat anti-rabbit IgG.

II. Electrophoretic Immunosubtraction

The analysis of M-proteins has been facilitated by electrophoretic methods. Such methods exploit the fact that proteins in solution have an intrinsic electrical charge. In the presence of an electric field, this intrinsic charge imparts a characteristic "electrophoretic" mobility to the protein, and thus permits various species of proteins to separate from one another. Under the influence of such a field, all of the proteins will move toward a designated electrode having a charge opposite to the charge of the proteins; those proteins having a lower electrophoretic mobility will move slower than, and hence be separated from, those proteins having a (relative) higher electrophoretic mobility.

Immunological electrophoretic methods, such as Immunofixation electrophoresis ("IFE"), Immunoelectrophoresis ("IEP"), and especially Immunosubtraction Electrophoresis ("ISE") have been used to classify and type M-proteins.

IEP and IFE are related procedures (Beckman Bulletin EP-2. "Immunoelectrophoresis Applications Guide." (1991)). IFE is a two stage procedure using agarose gel protein electrophoresis in the first stage and immunoprecipitation in the second. In a clinical setting for the analysis of immunoglobulins, a clinical sample (e.g., whole blood, serum, plasma, urine, cerebrospinal fluid) is placed in multiple positions ("lanes") on an agarose gel. Because immunoglobulins are proteins, they have a charge distribution such that when an electric field is applied to the gel-containing sample, the immunoglobulins will traverse the gel from anode to cathode. Thereafter, antisera comprising antibodies to specific immunoglobulin classes and types (typically IgG, IgA, IgM, kappa and lambda) are applied to specific lanes. The gel and antisera are incubated, during which time immune complexes form between the specific immunoglobulins and the antibodies. The location of such immune complexes are visualized by staining. By using a reference pattern on the gel, one can then determine the type of immunoglobulin present on the gel. The presence of a particular band is thus indicative of the presence of an M-protein corresponding to a particular immunoglobulin type. Methods of conducting IFE are disclosed by Chen, F-.T. A., U.S. Pat. No. 5,202,006; Chen, F-.T. A., U.S. Pat. No. 5,120,413; all herein incorporated by reference).

The PARAGON® electrophoresis system (Beckman Instruments, Inc., Fullerton, Calif., U.S.A.) is a commercially available system for conducting both IFE and IEP (See also, Gebott, et al., U.S. Pat. No. 4,669,363; Beckman Bulletin EP-3 "Paragon®Serum Protein Electrophoresis II (SPE-II) Applications Guide" (1990); Beckman Bulletin EP-2. "Immunoelectrophoresis Applications Guide" (1991); Beckman Bulletin EP-4 "Immunofixation Electrophoresis Applications Guide" (1991); Beckman Instructions 015-246513-H "Paragon® Electrophoresis System-IFE" (1990); Beckman Bulletin EP-6 "High Resolution Electrophoresis in the Detection of Monoclonal Gammopathies and Other Serum Protein Disorders." (1990); Chen, F-.T. A. et al. *Clin. Chem.* 37:14–19 (1991)).

Like immunoelectrophoresis, immunosubtraction electrophoresis (ISE) is a variation of IFE (Aguzzi, F. et al., *Estratto dal. Boll. 1st Sieroter, Milanese* 56:212–216 (1977); White, W. A. et al., *Biochem. Clin.* 10:571–574 (1986); Merlini, G. et al., *J. Clin. Chem. Biochem.* 21:841–844 (1983); Liu, C-.M. et al., U.S. Pat. No. 5,228,960, herein incorporated by reference). In ISE, however, the sample is pretreated with an insolubilized antibody directed to a particular "target" protein. If the target protein is present, it will bind to the antibody and thus be removed from the sample. The sample is then applied to a gel and subjected to electrophoresis. If the target protein had been present in the initial sample, visualization of the proteins in the gel would reveal a "negative band (i.e. an absence of staining) at the position in the gel where the removed band would have migrated to, had it not been removed by the antibody. Thus, the absence of a particular band is indicative of the presence of the corresponding target protein in the sample.

IEP, IFE and ISE thus each require multiple steps, and the preparation and use of a separation gel and a signal-generating stain. The labor intensive nature of these procedure is an obvious impediment in a clinical setting. Additionally, the amount of disposable end-products associated with these procedures can further increase the allied costs associated with these procedures.

In view of the deficiencies of these methods in clinical settings, less labor-intensive methods that permit greater throughput with lower cost have been sought. One such method is "Capillary Zone Electrophoresis" ("CZE") (Chen, F-.T. A., et al., *Clin. Chem.* 77:14–19 (1991); U.S. Pat. No. 5,120,413, both herein incorporated by reference). Capillary zone electrophoresis permits rapid and efficient separations of proteins (Grossman, P., et al., *Anal. Chem.* 61:1186–1194 (1989)), and other charged substances. Separation of the constituents of clinical samples can typically be accomplished in less than 20 minutes, typically in less than 10 minutes.

In general, CZE involves introducing a sample into a capillary tube, i.e. a tube having an internal diameter of from about 2 μm to about 200 μm (preferably, less than about 50 μm, most preferably, about 25μm or less), and applying an electric field to the tube. The electric potential of the field pulls the sample through the tube and separates it into its constituent parts. Since each of the sample constituents has its own individual electrophoretic mobility, those having greater mobility travel through the capillary tube faster than those with slower mobility. Hence, the constituents of the sample are resolved into discrete zones in the capillary tube during their migration through the tube. An on-line detector can be used to continuously monitor the separation and provide data as to the various constituents based upon the discrete zones.

CZE can be generally separated into two categories based upon the contents of the capillary columns. In "gel" CZE, the capillary tube is filled with a suitable gel, e.g., polyacrylamide gel, and separation of the constituents of the sample is thus predicated by both the size and the charge of the constituents. Despite the speed of analysis, gel CZE has several disadvantages, notably, the unpredictability and non-durable nature of the gel material. These factors make gel CZE unacceptable in any setting where numerous analytical runs are conducted.

In the second form of CZE (i.e. "open" CZE), the capillary tube is filled with an electrically conductive buffer solution (Kim, J. W. et al., *Clin. Chem.* 39:689–692 (1993)). The capillary tube is then ionized with a negative charge. Such ionization causes the capillary wall to become negatively charged, thereby attracts positive ions from the buffer. Because the electroneutrality of the solution must be maintained, any flow of positive ions towards the capillary wall will be accompanied by a similar movement of the buffer solution and the constituents of the sample. This electroendosmatic flow provides a fixed velocity component which drives both neutral species and ionic species, regardless of charge, towards the cathode. The buffer in "open CZE" is stable against conduction and diffusion. Accordingly, separations can be obtained in "open CZE" that are quite similar to those obtained in gel-based electrophoresis.

Fused silica is principally utilized as the material for the capillary tube because it can withstand the relatively high voltage used in CZE, and because the inner walls ionize to create the negative charge which causes the desired electroosmotic flow. However, alumina, beryllium, Teflon®-coated materials, glass, quartz and combinations of these (with or without fused silica) can also be utilized. The capillary column is typically capable of withstanding a wide range of applied electrophoretic fields of between about 10 v/cm to about 1000 v/cm. The capillary column may be coated on the outside (using, e.g., a polyimide material) for ease of handling. The inner wall of the capillary may be untreated or coated with a material capable of reducing adsorption to the inner wall during electroosmotic flow of the bulk solution. However, it is typically preferred that the inner wall be uncoated because typical coatings have a tendency to breakdown in an unpredictable manner. In U.S. Pat. No. 5,120,413, analysis of clinical samples was conducted using untreated capillary columns.

Open CZE has many desirable qualities ford e.g., clinical sample analysis: because the analysis does not involve a gel-filled column, the inherent limitations on the number of analytical runs that can be conducted with any particular gel-filled column are avoided; when the capillary column is untreated, the aura of unpredictability which can be associated with coated columns is avoided; the sample size is small (usually on the order of 5 to 200 nL of diluted sample); sample analysis time is fast, i.e. less than about 20 minutes; and the protocol lends itself to automation, thus decreasing the labor skills necessary for efficient and effective sample analysis.

Liu, C-.M. et al., U.S. Pat. No. 5,228,960, which has been incorporated by reference herein describes a recent modification to the CEI procedure that facilitates the classifying and typing of M-proteins. In the method, a portion of the sample is incubated with an insolubilized or insolubilizable binding partner that is capable of substantially removing M-protein from the solution, and then subjected to CZE. The "electropherogram" (i.e. a graphical representation of the separation of the constituent parts of the sample) of that portion is compared with that of an untreated sample. If the sample contains an M-protein, the electropherogram of the untreated sample will evidence the "complete" constituent profile of the sample; similarly, the electropherogram of the treated sample, when compared to the first, will evidence a "subtracted" peak corresponding to the M-protein that was removed from the sample.

As is evident, the method requires the use of a solid phase to effect the separation of the M-protein from the sample. The use of this heterogeneous system increases the incubation time of the sample, and therefore lowers the throughput of the analysis. It has not been possible to omit such a separation step because antibodies, and in particular, IgGs, the major serum immunoglobulins, co-migrate with heavy chain M-proteins. The amount of IgG in normal serum is larger than 20 mg/mL and the level of IgA and IgM is greater than 10 mg/mL. (see, for example, Roberts-Thomson, P. J. et al., *Austr. NZ J. Med.* 14:121–125 (1984)).

In view of the importance of accurately classifying and typing M-proteins, it would be desirable to possess a technique applicable to such analysis that would provide results with a minimum of processing steps, be easy to use, have high throughput and would avoid the end-product disposal problem occasioned by the use of separating gels.

SUMMARY OF THE INVENTION

The present invention provides such a method for classifying and typing M-proteins present in a sample of serum, etc. of an individual. More specifically, the method involves an improved method of on-capillary electrophoretic immunosubtraction to classify and type identified M-proteins.

In detail, the invention provides a method for the capillary electrophoretic analysis of a sample comprising at least one analyte as a constituent part, the method comprising the steps of:

(a) separating a first portion of the sample into constituent analyte parts by capillary electrophoresis, and detecting the parts;

(b) admixing a second portion of the sample with at least one specific binding partner to a predetermined candidate analyte, the specific binding partner having an electrophoretic mobility different from that of analyte;

(c) separating the second portion into constituent parts by capillary electrophoresis, and detecting the parts; and, (d) comparing the separated constituent parts of step (c) with the separated constituent parts of step (a).

The invention also provides a method for the capillary electrophoretic analysis of a sample comprising at least one constituent part comprising the steps of:

(a) simultaneously separating: a first aliquot of the sample into constituent parts by capillary electrophoretic techniques, and detecting the parts; and a second aliquot of the sample into constituent parts, the second aliquot having been admixed with at least one specific binding partner to a constituent of the sample, the specific binding partner having an electrophoretic mobility different from that of the constituent part of the specific binding partner; and, (b) comparing the separated constituent parts of the first aliquot with the separated constituent parts of the second aliquot.

The invention is further directed to the embodiments wherein the sample is selected from the group consisting of whole blood, plasma, serum, urine and cerebrospinal fluid, or wherein the predetermined candidate analyte is an immunoglobulin (especially an M-protein).

The invention particularly concerns the embodiments of the above methods wherein the specific binding partner is an antibody, modified (especially by reaction with an anhydride) to have an electrophoretic mobility different from that of the analyte to which it binds or an analyte-binding fragment of an antibody.

The invention also provides an acylated anti-human immunoglobulin antibody having an electrophoretic mobility different from that of human immunoglobulin.

DESCRIPTION OF THE PREFERRED EMBODIMENTS

Figure 1:
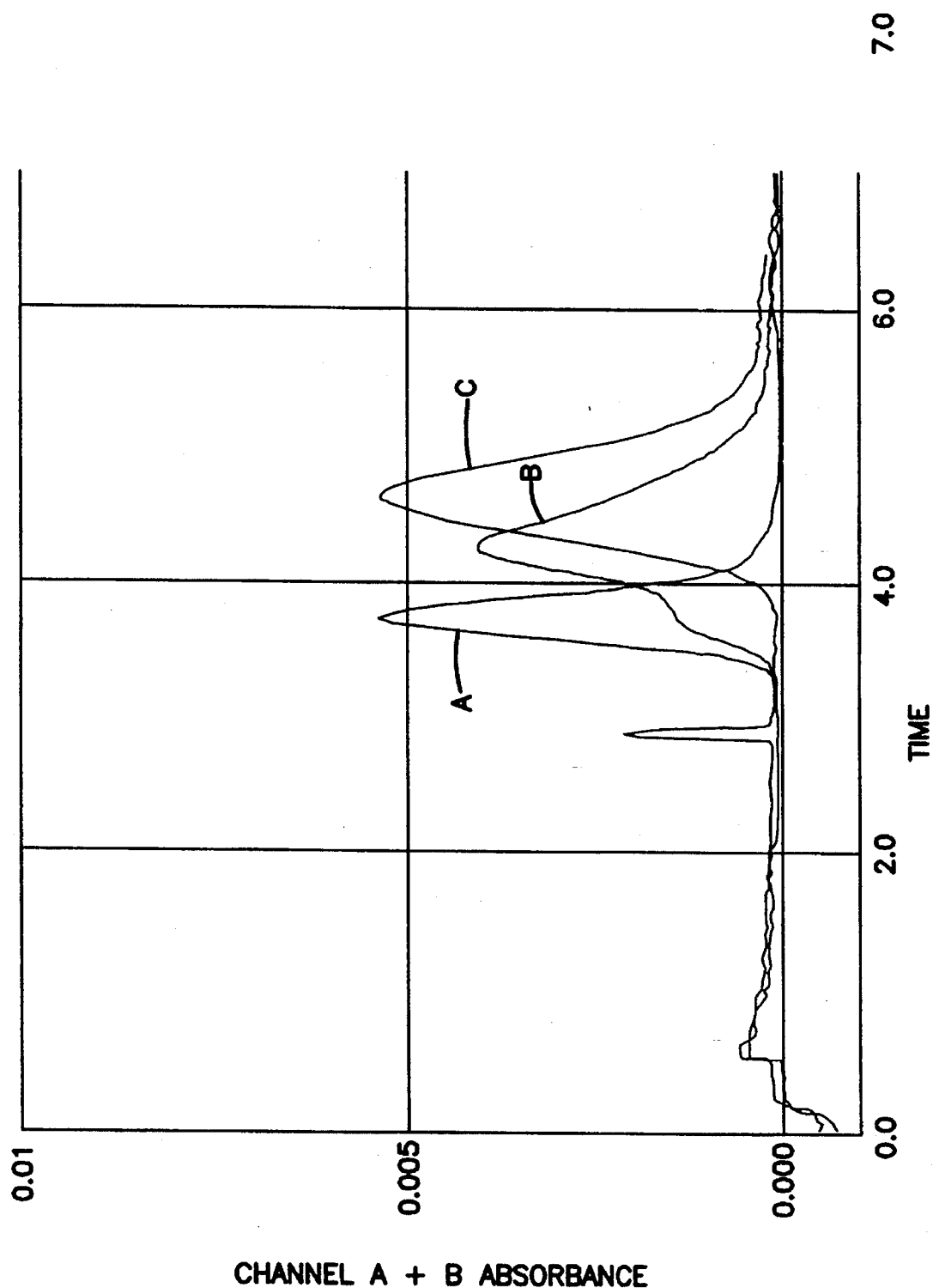
FIG. 1 is a representation of an electropherogram. Curve a provides a representation of the electropherogram of unmodified IgG; Curve b provides a representation of the electropherogram of modified IgG; Curve c provides a representation of the electropherogram of a sample having an IgG M-protein after incubation with modified anti-IgG antibody.

The present invention provides an improved method of "Capillary Electrophoretic Immunosubtraction ("CEI"). The method can be used to analyze any soluble sample substituent, and is particularly able to classify and type M-protein in a sample.

As stated above, the fact that M-protein co-migrates with IgG (i.e., migrates in the "gamma region" of the column) has previously required a "removal" (or insolubilization) step in order to analyze the M-protein of a patient. Liu, C-.M. et al., U.S. Pat. No. 5,228,960, solved this problem using a heterogeneous electrophoresis assay system.

The CEI procedure of the present invention uses a "modified" analyte binding molecule that, despite such modification retains its ability to bind to M-protein, serum protein, etc. (i.e. to a predetermined "analyte"). The use of the modified analyte binding molecule permits the CEI procedure to be performed in a (preferably aqueous) homogeneous phase without any need for insolubilizing the complexed analyte. The analyte binding molecule is most preferably an antibody (either monoclonal or polyclonal). It may, alternatively, be a fragment of such an antibody (such as an Fab or F(ab)$_2$ fragment), or may be a recombinant or "single-chain" antibody. As used herein, an anti-human immunoglobulin antibody is an antibody (human or non-human) that is capable of specific binding with a human immunoglobulin. Suitable anti-M-protein antibodies are commercially available from DAKO Corporation (Copenhagen, Denmark), and from Behringewerke AG (Marburg, Germany). Alternatively, polyclonal antibodies can be obtained by purifying M-protein and using it to elicit polyclonal antibodies from a rabbit or other mammal. Similarly, monoclonal antibodies may be derived and used. For ease of reference below, the binding molecule will be described as an antibody.

The method of the present invention further eliminates the need of a solid phase, eliminates the separation step required to remove bound antigen, enhances the immunoreaction by using a liquid phase antibody, and reduces the amount of antibody required for each immunosubtraction.

In accordance with the present invention, the analyte-specific antibody is chemically modified such that its migration time on capillary electrophoresis that is no longer in the gamma region. Any method for altering the typical co-migration of the anti-analyte antibody may be employed. Most preferably, the antibody is modified to increase its mobility to the anode (i.e. to retard its mobility toward the cathode).

Any of a variety of methods can be used to effect such modification. Most preferably, however, the antibody is chemically modified using an anhydride (such as succinic anhydride) to alter its electrophoretic mobility. Succinic anhydride is very reactive to the primary amino groups, such as lysine epsilon amino groups in immunoglobulins. For example, each heavy chain immunoglobulin molecule contains approximately 50 lysine residues. In effecting the modification of these groups with succinic anhydride, it is desirable to obtain a modification sufficient to cause a change in electrophoretic mobility, yet not so extensive as to unacceptably impair the capacity of the antibody to bind to the analyte.

A preferred modification procedure thus involves incubating an anti-human immunoglobulin (i.e. anti-IgG, anti-IgA, anti-IgM, anti-K or anti-X) in the presence of an anhydride for 30–60 minutes with gentle agitation. The reaction mixture is then dialyzed against an aqueous buffer, and can then be used in accordance with the methods of the invention.

In one embodiment of the present invention, capillary electrophoresis is then used to separate an untreated portion of a sample into its constituent parts. A second portion of the sample is incubated with the modified analyte-specific antibody, and then subjected to capillary electrophoresis.

In such an embodiment, the capillary electrophoretic analyses of such untreated and treated samples are compared. Although such comparison can be accomplished in a variety of substantially equivalent ways, it is most preferably accomplished by generating and comparing electropherograms of the analyzed samples. For example, a constituent which is present in a sample in a high concentration may evidence a peak having a large height and wide width compared to a constituent present in a (relatively) low concentration. Typically, the electropherogram is derived by plotting detection units (such as UV absorbance) on the vertical axis, and time of constituent traversal through the column to a detection region on the horizontal axis. Fluorescence-based detection assays have also been described (Lee, T. T. et. al., *J. Chromatogr.* 595:319–325 (1992)). Results can also be derived in terms of a unit value, typically derived from the areas bounded by the individual peaks. If the sample contains M-protein, the electropherogram of untreated sample will evidence the "complete" constituent profile of the sample; similarly, the electropherogram of the treated sample, when compared to the first, will evidence a "disappearance" (i.e. diminution or absence) of a peak from the gamma region in consequence of the use of the modified antibody.

In an alternative embodiment of the present invention, the sample is incubated with the modified analyte-specific antibody, and then subjected to capillary electrophoresis. In this embodiment, the classification and typing of the analyte is accomplished without reference to the electropherogram of an untreated sample. Thus, rather than determining whether a peak disappears from the gamma region, one ascertains whether a peak—representing the immune complex formed by the analyte-specific antibody—is detectable outside the gamma region. The two embodiments can be combined to provide enhanced accuracy in classifying and typing the analyte.

The nature of the antibody used characterizes the class or the type of immunoglobulin of that peak. Thus, for example, if the use of a succinylated anti-IgA antibody caused a peak to disappear from the gamma region of the column, then the particular M-protein of the patient would be classified as an IgA M-protein. In a similar manner, use of an anti-K antibody would reveal whether the patient had a K type M-protein. Although it is preferred to use only one modified antibody per CEI procedure, it is possible, by adjusting the extent of modification to simultaneously employ two or more modified antibodies (such as an anti-IgA and an anti-IgG) in the same reaction. All that is required for such a modification is that each such antibody has an electrophoretic mobility that (1) differs from IgG and (2) differs from one another. Such modified antibodies can be obtained by varying the extent of modification.

As indicated, evaluation of the CEI methods of the present invention is typically visually oriented, i.e. the electropherograms of untreated samples are evaluated to determine whether new peaks are formed and/or compared with the electropherograms of treated samples to discern whether any peak has disappeared. The areas beneath each constituent peak can also be compared; i.e. with the exception of the area beneath "subtracted" peak, the numerical area values beneath the individual peaks from the first and second aliquots are substantially the same, while the numerical are a beneath the region of the immunosubtracted M-protein from the treated sample will be substantially different than the corresponding area for the untreated sample. In sum, the absence of an M-protein peak in the treated sample indicates that the sample being analyzed Contained M-protein, and further permits the quantification of the M-protein concentration in the original sample.

In order to compare two electropherograms (or the comparative areas beneath the peaks), it is preferred that the electropherograms be normalized. Typically, normalization involves three steps: (1) baseline normalization; (2) absorbance normalization; and (3) time normalization.

Baseline normalization is typically accomplished by adjusting the electropherograms such that each has a common horizontal baseline; beneficially, this merely requires shifting upward or downward the entire electropherogram in the case where the initial baseline is below or above the zero axis, respectively. Baseline normalization allows for creation of a common horizontal axis.

Absorbance normalization is preferably based upon the most prevalent protein component in serum, albumin. Typically, the electropherogram peak associated with albumin is the "tallest" peak. By selecting a single absorbance maximum for the albumin peak, all of the peaks within the electropherogram will be proportionately adjusted. Absorbance normalization thus rectifies differences in, for example, the respective amounts of the treated and untreated sample being analyzed. Preferably an absorbance maximum for albumin is between about 0.10 and about 0.20 absorbance units, most preferably about 0.15. In lieu of using albumin concentration, the absorbance normalization can be accomplished using a marker, or any other constituent common to both the treated or untreated samples Time normalization is principally accomplished in order to place the resulting electropherogram results within a constant region. Preferably, this is accomplished by the use of two "markers" which are added prior to the analysis of the treated and untreated samples. The markers are selected such that they are capable of traversing the capillary column and being detected at respective times that bracket the detection times of the sample constituents. Thus, if the detected sample constituents are detected at different times (due to, e.g., variability in the amount of sample analyzed), the relative detection times of the two sets of constituents can be normalized using the markers.

Most preferably, the two markers are prepared as follows: 20 mg of dichlorobenzoic acid is dissolved into dimethylformamide and this mixture is added to 100 ml of an appropriate buffered solution, such as ICS™ diluent (Beckman Instruments, Inc.). Aliquots of this solution are then added to the treated and untreated samples, such that they will contain the same relative concentrations of markers. During analysis, these markers traverse the column along with the sample constituents. The electrophoretic mobilities are such that the dimethylformamide peak will typically appear as the "first" detected peak, followed by the sample constituents, then followed by the "last" detected peak, dichlorobenzoic acid. Thus, the peaks attributed to the sample constituents are bracketed by the two markers.

In an alternative embodiment of such time normalization, the markers may be selected such that they will bracket the position of the analyte-antibody complex.

Time normalization, like absorbance normalization, is accomplished such that the relative areas beneath the individual electropherogram peaks remain the same; such normalization merely allows the two electrophorograms to be accurately compared to each other. Methodologies for such time normalization are disclosed by F-.T. A. Chen, U.S. Pat. No. 5,139,630, which is incorporated fully herein by reference. Methods for improving signal-to-noise ratios in electropherograms are disclosed by Anderson, P. D., U.S. Pat. No. 5,098,536, herein incorporated by reference.

An alternative approach to the analysis, which is also visually oriented, is based upon the manner in which slab-gel IFE results are derived, i.e. bands at the location of the M-protein. Methods and apparati for converting electropherogram peaks into such bands are disclosed in copending U.S. Ser. No. 07/911,307 entitled "Method and Apparatus for Displaying Capillary Electrophoresis Data" by Gerald L. Klein and Steven P. Katzman, which is incorporated herein by reference.

Although the above-description has focused upon serum as a sample, any of a variety of samples can be analyzed. Preferably, the sample is a clinical sample (such as whole blood, serum, plasma, urine, cerebrospinal fluid, etc.). It is preferred that such clinical samples be diluted prior to analysis; such dilution, facilitates inter alia achieving a desired analytical ratio, and further augments the sensitivity of the analysis. I.e., a non-diluted clinical sample, particularly serum, may contain too much protein to permit accurate analysis. Focusing on serum, a most preferred dilution is a one part serum to ten parts of an appropriate diluent, however, dilution of up to one part serum to about 100 parts diluent can also be used. The diluent is preferably a lightly buffered saline solution, pH 7.0, such as the ICS™ diluent.

The ratio of the specific binding partner to the sample constituent of interest is principally selected with respect to two factors. First, such binding partner(s) is preferably provided at a concentration sufficient to substantially remove all of the M-protein that may be expected to be present in the sample. Second, the loading efficiency of the binding partner onto the solid support is considered. This second factor reflects a concern over the cost:benefit ratio since overloading the binding partner can increase cost without increasing the amount of constituent binding. The ratio of specific binding partner to M protein is preferably between about 1:1 to about 15:1.

A variety of capillary tubes or columns can be used in accordance with the present invention. Such columns can be untreated (i.e. having the inner walls of "bare" fused silica or the like) or can be coated with an appropriate material. Coated capillaries have enjoyed widespread use in the area of capillary electrophoresis, principally because these coatings tend to limit protein adsorption to the untreated walls during the electrophoretic separation procedure. However, eventually these coatings will breakdown in an unpredictable manner. Therefore, while the disclosed CEI protocol can be used with either untreated or coated columns, it is preferred that the columns be untreated. When untreated capillary columns are utilized, preferably the separation buffer is as disclosed in U.S. Pat. No. 5,120,413, herein incorporated by reference. Suitable columns are further disclosed by Guttman, A., U.S. Pat. No. 5,213,669; Burolla, V. P., U.S. Pat. No. 5,198,091; Shieh, C-.H., U.S. Pat. No. 5,098,539; all herein incorporated by reference.

Most preferably, the buffer is 150 mM borate, pH 10.00±0.25; concentrations between about 70 mM and about 400 mM are, however, viable. As the molarity of the buffer increases, the temperature inside the column can increase, and thus, in situations where temperature effects upon the constituents are a factor, lower concentrations of the buffer should be utilized. However, it is to be understood that the disclosed CEI protocol can be accomplished with any separation buffer used in conjunction with the separation of proteinaceous materials using coated or untreated columns.

Capillary electrophoresis instrumentation systems that can be used in conjunction with the CEI procedures of the present invention are well known. A particularly preferred instrument is a multi-channel apparatus that allows simultaneous evaluation of at least two different aliquots of sample; more preferably, the apparatus has the capability of analyzing several aliquots simultaneously such that multiple electropherograms can be obtained and compared. A particularly preferred capillary electrophoretic system is disclosed in copending U.S. Ser. No. 07/916,308 entitled "Multichannel Automated Capillary Electrophoresis System" by Gerald L. Klein, which is incorporated herein by reference. For research evaluation and validation, a particularly preferred capillary electrophoretic system is the P/ACE™ high performance capillary electrophoresis system (Beckman Instruments, Inc.) (Chen, F-.T. A., *Clin. Chem.* 38:1651–1953 (1992); Chen, F-.T. A., *J. Chromatogr.* 559:445–453 (1991); Fu, P. C. et al., *Clin. Chem.* 37:970 (1991); Chen, F-.T. A., *Clin. Chem.* 37:1061 (1991); Gordon, M. J. et al., *Anal. Chem.* 63:69–72 (1991), all also herein incorporated by reference). Such instruments are most preferred in that normalization of the electropherograms can be accomplished via on-board computer software (such as System Gold™ software (Beckman Instruments, Inc., Fullerton, Calif., USA).

In one embodiment of such multichannel analysis the identification of M-protein presence is conducted in parallel with analyses of other sample constituents, such as IgG, IgA, IgM, and the kappa and lambda chains of immunoglobulins. Such an embodiment permits a single analytical evaluation of multiple constituents in the sample.

Having now generally described the invention, the same will be more readily understood through reference to the following examples which are provided by way of illustration, and are not intended to be limiting of the present invention, unless specified.

EXAMPLE 1

ON-CAPILLARY ELECTROPHORETIC IMMUNOSUBTRACTION FOR CLASSIFICATION AND TYPING OF M-PROTEINS

To determine whether a sample contained IgG class M-protein, on-capillary immunosubtraction was performed. The sample was incubated with a modified anti-IgG antibody, and subjected to capillary electrophoresis.

Experimental

1. Electropherogram Mobility of Unmodified Anti-IgG Antibody

The anti-IgG antibody was electrophoresed in 150 mM borate buffer (pH 10.0), in an untreated fused silica open capillary (i.d. 25 u, and 20 cm separation length) at a voltage of 10 kV and at a temperature of 24° C. The antibody was found to migrate, as expected, in the gamma region of serum protein electropherogram.

2. Modification of the Anti-IgG Antibody with Succinic Anhydride a) Goat anti-human IgG (10 mg/ml from DAKO Corporation (Copenhagen, Denmark)) was dialyzed against phosphate buffered saline (0.15M, pH 7.2) with three changes of buffer at a volume ratio of 1:1,000 each.

b) 10 mg of succinic anhydride was dissolved in 100 µl of dimethyl formamide.

c) 6.7 µl of the succinic anhydride solution was mixed with 200 µl of distilled water.

d) The dialyzed goat anti-human IgG was diluted to 5 mg/ml and then mixed with the diluted succinic anhydride solution.

e) The mixture was mixed for 30 to 60 minutes with an inverting mixer.

f) The reaction mixture was dialyzed against PBS as described in Step 1.

g) The dialyzate was then ready to use as succinylated goat anti-human IgG antibody.

3. Electropherogram Mobility of Succinylated Anti-IgG Antibody

The succinylated anti-IgG antibody was subjected to electrophoresis as described in Step 1, and was found to be more anodic than the unmodified one.

4. Identification and characterization of Immunoglobulin using On-capillary Immunosubtraction An immunoglobulin sample was electrophoresed in the capillary under the conditions described in Step 1. As illustrated in the representation of an electropherogram in FIG. 1, curve a, the immunoglobulin appeared in the gamma region. Similarly, an electrophoreogram was obtained for succinylated goat anti-human IgG as illustrated in curve c of FIG. 1. One (1) ml of the immunoglobulin sample was then mixed with 6.7 µl of the succinylated anti-IgG antibody solution. The reaction mixture was incubated for 1-60 minutes at ambient temperature, and subjected to capillary electrophoresis using the same conditions. The results are illustrated in FIG. 1, curve b: the peak is that of an immunoglobulin:anti-IgG antibody complex, indicating the formation of an immune complex. The shoulder of the complex peak in curve b indicates a small amount of uncomplexed IgG in the sample in which the succinylated anti-IgG:IgG complex was formed.

The disappearance of a peak from the gamma region characterized the class or the type of immunoglobulin of that peak, i.e., because the succinylated anti-IgG antibody was monospecific to IgG, the immunoglobulin in the sample was characterized as IgG. This method eliminated the need of a solid phase, eliminated the separation step required to remove the bound antigen, enhanced the immunoreaction by using a liquid phase antibody, and reduced the amount of antibody required for each immunosubtraction. By using this approach, serum M-proteins could be classified (IgA, IgG, IgM, etc.) and typed by their light chain composition (kappa and lambda).

In sum, classification and typing of human serum M-protein has been performed using an analyte specific antibody which has been chemically modified with succinic anhydride such that its migration time on capillary electrophoresis is no longer in the gamma region while retaining its binding activity to its antigen analyte.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for capillary electrophoretic analysis of a sample comprising at least one analyte as a constituent part, said method comprising the steps of:

(a) separating a first portion of the sample into constituent analyte parts by capillary electrophoresis, and detecting said parts;

(b) admixing a second portion of said sample with at least one specific binding partner to a predetermined candidate analyte, said specific binding partner having an electrophoretic mobility different from that of said candidate analyte;

(c) separating said second portion into constituent parts by capillary electrophoresis, and detecting said parts; and, (d) comparing the separated constituent parts of step (c) with the separated constituent parts of step (a).

2. The method of claim 1, wherein said sample is selected from the group consisting of whole blood, plasma, serum, urine and cerebrospinal fluid.

3. The method of claim 1, wherein said predetermined candidate analyte is an immunoglobulin.

4. The method of claim 3, wherein said immunoglobulin is an M-protein.

5. The method of claim 4, wherein said M-protein has a heavy chain selected from the group consisting of IgA, IgG, IgM, IgD, and IgD.

6. The method of claim 5, wherein said M-protein has a light chain selected from the group consisting of kappa and lambda.

7. The method of claim 1, wherein said specific binding partner is an antibody, and wherein said antibody has been modified to have an electrophoretic mobility different from that of IgG.

8. The method of claim 7, wherein said antibody is a monoclonal antibody.

9. The method of claim 1, wherein said specific binding partner is an analyte-binding fragment of an antibody.

10. The method of claim 7, wherein said antibody has been modified by reaction with an anhydride.

11. The method of claim 10, wherein said anhydride is succinic anhydride.

12. The method of claim 1 wherein the detected constituent parts of step (a) and (c) are normalized.

13. The method of claim 1, wherein the ratio of specific binding partner to said constituent is between about 1:1 and about 15:1.

14. A method for capillary electrophoretic analysis of a sample comprising at least one constituent part comprising the steps of:

(a) simultaneously separating: a first aliquot of the sample into constituent parts by capillary electrophoretic techniques, and detecting said parts; and a second aliquot of the sample into constituent parts, said second aliquot having been admixed with at least one specific binding partner to a constituent of said sample, said specific binding partner having an electrophoretic mobility different from that of said constituent to which said binding partner binds; and, (b) comparing the separated constituent parts of the first aliquot with the separated constituent parts of the second aliquot.

15. The method of claim 14, wherein said sample is selected from the group consisting of whole blood, plasma, serum, urine and cerebrospinal fluid.

16. The method of claim 14, wherein said predetermined candidate analyte is an immunoglobulin.

17. The method of claim 16, wherein said immunoglobulin is an M-protein.

18. The method of claim 17, wherein said M-protein has a heavy chain selected from the group consisting of IgA, IgG, IgM, IgE, and IgD.

19. The method of claim 18, wherein said M-protein has a light chain selected from the group consisting of kappa and lambda.

20. The method of claim 14, wherein said specific binding partner is an antibody, and wherein said antibody has been modified to have an electrophoretic mobility different from that of IgG.

21. The method of claim 20, wherein said antibody is a monoclonal antibody.

22. The method of claim 14, wherein said specific binding partner is an analyte-binding fragment of an antibody.

23. The method of claim 22, wherein said antibody has been modified by reaction with an anhydride.

24. The method of claim 23, wherein said anhydride is succinic anhydride.

25. The method of claim 14, wherein the ratio of specific binding partner to said constituent is between about 1:1 and about 15:1.

* * * * *